(12) United States Patent
De Boer et al.

(10) Patent No.: US 10,041,875 B2
(45) Date of Patent: Aug. 7, 2018

(54) APPARATUS AND METHOD FOR READING OUT AN OPTICAL CHIP

(71) Applicant: Nederlandse Organisatie voor toegepast-natuurwetenschappelijk onderzoek TNO, 's-Gravenhage (NL)

(72) Inventors: Bart Michiel De Boer, 's-Gravenhage (NL); Peter Johan Harmsma, 's-Gravenhage (NL); Dario Maria Rosario Lo Cascio, 's-Gravenhage (NL)

(73) Assignee: Nederlandse Organisatie voor toegepast-natuurwetenschappelijk onderzoek TNO, 's-Gravenhage (NL)

( * ) Notice: Subject to any disclaimer, the term of this patent is extended or adjusted under 35 U.S.C. 154(b) by 149 days.

(21) Appl. No.: 15/301,749

(22) PCT Filed: Mar. 31, 2015

(86) PCT No.: PCT/NL2015/050207
§ 371 (c)(1),
(2) Date: Oct. 4, 2016

(87) PCT Pub. No.: WO2015/152717
PCT Pub. Date: Oct. 8, 2015

(65) Prior Publication Data
US 2017/0115206 A1    Apr. 27, 2017

(30) Foreign Application Priority Data

Apr. 4, 2014    (EP) .................................... 14163611

(51) Int. Cl.
*G01N 21/03*    (2006.01)
*G01N 21/05*    (2006.01)
*G02B 6/34*    (2006.01)

(52) U.S. Cl.
CPC ......... *G01N 21/0303* (2013.01); *G01N 21/05* (2013.01); *G02B 6/34* (2013.01);
(Continued)

(58) Field of Classification Search
CPC .............................. G01N 21/0303; G02B 6/34
See application file for complete search history.

(56) References Cited

U.S. PATENT DOCUMENTS

| 5,907,649 | A | 5/1999 | Acklin et al. |
| 5,926,594 | A * | 7/1999 | Song ........................ G02B 6/30 385/15 |
| 7,378,861 | B1 | 5/2008 | Malendevich et al. |

FOREIGN PATENT DOCUMENTS

EP    0866329 A2    9/1998

OTHER PUBLICATIONS

Jun. 24, 2015—International Search Report and Written Opinion of PCT/NL2015/050207.

* cited by examiner

*Primary Examiner* — Renee Chavez
(74) *Attorney, Agent, or Firm* — Banner & Witcoff, Ltd.

(57) ABSTRACT

The present disclosure concerns an apparatus (10) and method for reading out an optical chip (20). A light source (13) is arranged for emitting single mode source light (S1) from its emitter surface (A1) towards an optical input (21) of the optical chip (20). A light detector (14) is arranged for receiving measurement light (S2) impinging onto its receiver surface (A2) from an optical output (22) of the optical chip (20), and measuring said received measurement light (S2). The emitted source light (S1) is aligned to enter the optical input (21) of the optical chip (20) and the measurement light (S2) is aligned back onto the receiver (Continued)

surface (A2). The receiver surface (A2) is larger than the emitter surface (A1) for facilitating the overall alignment.

15 Claims, 6 Drawing Sheets

(52) U.S. Cl.
CPC ................ *G01N 2021/0321* (2013.01); *G01N 2021/0367* (2013.01); *G01N 2201/06* (2013.01); *G01N 2201/0873* (2013.01)

APPARATUS AND METHOD FOR READING OUT AN OPTICAL CHIP

CROSS-REFERENCE TO RELATED APPLICATIONS

This application is a U.S. National Stage application under 35 U.S.C. § 371 of International Application PCT/NL2015/050207 (published as WO 2015/152717A1), filed Mar. 31, 2015, which claims priority to Application EP 14163611.8, filed Apr. 4, 2014. Benefit of the filing date of each of these prior applications is hereby claimed. Each of these prior applications is hereby incorporated by reference in its entirety.

TECHNICAL FIELD AND BACKGROUND

The present disclosure relates to an apparatus and method for reading out an optical chip.

Optical structures such as ring resonators can be employed as sensors on an optical chip to detect one or more measurement parameters such as pressure, refractive index, presence of biomolecules, etcetera. These sensors can be part of an integrated optical circuit forming the optical chip. Typically, the optical circuit is externally addressable via an optical input and/or output. The sensor response can e.g. be measured by coupling source light into the optical input of the chip and collecting light from the optical output. While traversing the optical circuit, a property of the source light, e.g. intensity, can be modulated by interaction with the optical sensor, which interaction can be dependent on a measurement parameter. The measurement light collected from the optical output can be analysed and translated to yield an absolute or relative value of the parameter. Accordingly, the optical chip can be read out by coupling light into and out of the optical chip.

The coupling of source light into the chip as well as read-out and analysis of the measurement light received back is typically performed by an apparatus, also referred to as an analyser, that is specifically adapted to read out the chip, e.g. determine the measurement parameters of the chip. In case of employment as biosensors, e.g. as point-of-care diagnostic tests, a robust and cost effective coupling between the analyser and the sensor is desired that can be established in minimal time, e.g. seconds. Moreover, since these are typically disposable sensors, the coupling should preferably not add to the cost of the sensor too much.

One method to couple light into and out of an optical chip comprises the establishment of a permanent physical connection of optical fibres to the optical input and output ports of the chip, e.g. by adhesion or standard fibre connectors. However, for disposable sensor chips, such a permanent connection is too expensive because of labour and material costs. Furthermore, the connection may be fragile, e.g. the connected fibres may break. Accordingly, it is desired to avoid physical connections to and from the optical ports of the chip.

Another method to couple light into and out of an optical chip comprises illumination of one part of the chip with a broad beam and receiving light back from different location on the chip using a pixel array (camera). This method has the advantage that no physical connection to the optical ports of the chip is required. However, typically the optical chip accepts only a limited number of modes or even a single mode. Therefore, most of the broad light beam cannot enter the input port, and is lost. Furthermore, since most of the pixels are not used, pixel array is inefficient in collecting the light. Furthermore, the pixel array can be relatively expensive. Accordingly it is desired to provide a single in/out combined optical connection to efficiently irradiate and collect the light to and from the optical chip.

Yet another method to couple light into and out of an optical chip comprises bringing an array of input and output fibres close to the chip surface and holding them there during the sensor measurement. This method provides a cost benefit because it does not require physical connection to the optical ports of the chip. Furthermore this method can make relatively efficient use of the light because the fibre inputs and output can be targeted to specifically couple light to and from the optical ports. However, it can be difficult to establish an alignment between the optical fibres and optical ports of the chip, and the system may easily be damaged while inserting a new disposable chip.

For example, U.S. Pat. No. 5,926,594 describes a system for aligning and attaching optical fibers to optical waveguides in an integrated optic chip. Optical couplings to the waveguide legs include an input optical fibre positioned adjacent waveguide input leg, and a pair of output optical fibres respectively positioned adjacent the waveguide output legs. Light outputted from output optical fibres is directed respectively to different detectors, i.e. each fibre corresponds to different detection channel. Unfortunately, alignment of the system is rather complex involving a service robot, further alignment robots, an alignment plate, precision alignment pins, pre-alignment pins, and a goniometer.

For example, U.S. Pat. No. 7,378,861 B1 describes, wafer designs, testing systems and techniques for wafer-level optical testing by coupling probe light to/from the top of the wafer. A wafer level test system uses an optical probe to search for and aligning with an optical alignment loop. The test system uses a located alignment loop as a reference point to locate other devices on the wafer. A fine yaw optimization mechanism based on a yaw adjustment in the optical probe positioner and an alignment loop on the wafer may be implemented and operated in combination to address the alignment issue of a fibre array. However, the described alignment strategy may require dedicated structures on the wafer as well as a dedicated fibre probe which is not cost effective. Furthermore, the alignment is time consuming and requires sensitive actuators to coordinate the alignment of the plurality of the optical ports simultaneously.

Accordingly, a desire remains for an apparatus and method for reading out an optical chip that obviates one or more of the above discussed disadvantages while maintaining the advantages. In particular, it is desired to establish an efficient, robust, and cost effective optical coupling between the apparatus and optical chip in minimal time.

SUMMARY

A first aspect of the present disclosure provides an apparatus for reading out an optical chip, the apparatus comprising a chip holder arranged for receiving and holding the optical chip; a light source comprising an emitter surface, said light source arranged for emitting single mode source light from said emitter surface towards an optical input of the optical chip held by the chip holder; a light detector comprising a single channel receiver surface arranged for receiving measurement light impinging onto said receiver surface from an optical output of the optical chip held by the chip holder, and measuring said received measurement light; an alignment system arranged for controlled movement of the chip holder relative to the emitted source light for aligning the emitted source light from the light source to enter the optical input of the optical chip and for aligning the measurement light from the optical output of the optical chip back onto the receiver surface for measuring the measurement light; wherein the receiver surface is larger than the emitter surface.

By contactless transfer of the optical signals from the emitter surface to the optical input and from the optical output back to the receiver surface, the connection can be robust and cost effective. By using single mode source light emitted from a relatively small emitter surface, the light can be efficiently coupled into the optical input of the chip, e.g. via a grating coupler. By using a light detector with a single channel receiver surface, the measurement light from the chip can be efficiently collected and in a cost effective manner. The single channel receiver surface collects or combines the impinging light for measurement in a single detection channel. By providing a receiver surface or aperture larger than the emitter surface or aperture, overall alignment can be facilitated because only the optical input needs accurate alignment with respect to the relatively small emitter surface or aperture while the alignment of the optical output can be less sensitive. Advantageously, the receiver surface or aperture can have a multi-mode character. For example, the alignment of the plurality of optical ports can be faster because after establishing a translational alignment of the optical input, the one or more optical outputs are either automatically aligned or can be easily brought into alignment with a relatively coarse rotation of the optical chip around the optical input. Preferably the receiver surface or aperture is at least twice as large as the emitter surface or aperture By providing a receiver surface or aperture arranged for receiving optical signals from a relatively large solid angle compared to the emitter surface or aperture, collection efficiency of the measurement light from the optical chip can be increased. It will be appreciated that a relatively large acceptance of the light detector via the receiver surface or aperture may increase the ability to collect the measurement light when it is only emitted from the optical output at a particular angle, e.g. when the optical output comprises a grating coupler. In the case of on-chip grating couplers, the emission angle from the grating coupler is wavelength dependent. A receiving surface or aperture which accepts a large solid angle will therefore accept a broader range of wavelengths, enabling optical measurements over a broader optical bandwidth, at a transmission efficiency with reduced wavelength dependence.

By providing an imaging system between the emitter/receiver surfaces and the optical chip, the optical signals can be more efficiently transferred therein between over a larger distance. It will be appreciated that by increasing the distance, accidental, potentially damaging contact between the optical chip and the emitter/receiver surfaces can be avoided.

The solid angle over which the receiver surface can receive light via the imaging system defines an effective acceptance of the light detector which may be limited e.g. by an edge of a lens in the imaging system. The solid angle over which the emitter surface can send light via the imaging system defines an effective optical extent of the light source which may be similarly limited e.g. by an edge of a lens in the imaging system. By providing an effective acceptance of the light detector that is larger than the effective optical extent of the light source, optimal transmission is achieved over a large optical bandwidth.

By emitting the source light of the light source via an optical fibre, a position and direction of the emitter surface, which in case of an optical fibre is formed by an end surface of the optical fibre, can be more easily adjusted. Similarly, by receiving the measurement light to the light detector via an optical fibre, a position and direction of the receiver surface, which in case of an optical fibre is formed by an end surface of the optical fibre, can be more easily adjusted. Advantageously, when both the source light and measurement light travel via optical fibres, the fibres can be comprised in a fibre array or interface. By fixing a relative position of the fibres, a relative alignment of the emitter and receiver surfaces with respect to the optical input and outputs can be facilitated.

Advantageously, a single-mode (SM) optical fibre can be used to emit the single mode source light from the light source to the optical input. By using a single-mode optical fibre, the optical mode, e.g. directionality and spot size, of the source light can be accurately adapted to the optical input of the chip Advantageously, a multi-mode (MM) optical fibre can be used to receive the measurement light from the optical output and transfer the signal to the light detector. It will be appreciated that a multi-mode optical fibre generally has a larger end surface than a single-mode optical fibre. Accordingly, a combination of a single mode optical fibre as emitter of the source light and a multi-mode optical fibre as receiver of the measurement light is considered an advantageous embodiment.

It will be appreciated that the optical chip may comprise a plurality of the optical outputs connected to the optical input via an optical circuit, for example an arrangement of sensor elements. The apparatus may accordingly comprise a plurality of single channel receiver surfaces, for example a plurality of the optical fibres, each connected to a respective light detector. By providing a plurality of the optical outputs/receiver surfaces, a plurality of measurement light can be measured simultaneously. By having each of the receiver surfaces larger than the emitter surface, overall alignment can be facilitated because only the optical input needs accurate alignment with respect to the relatively small emitter surface while the alignment of the plurality of the optical outputs can be less critical, e.g. achieved automatically or by relatively coarse rotation after the optical input is aligned.

As opposed to the optical source signal, the received optical signals have a multi-mode rather than a single-mode character. This limits the options for further optical signal processing. Generally, received signals may be incident on detectors which accept multi-mode signals, wherein further signal processing is done in the electrical domain.

A second aspect of the present disclosure provides a method for reading out an optical chip, the method comprising receiving and holding the optical chip; providing a light source comprising an emitter surface, said light source arranged for emitting single mode source light from said emitter surface towards an optical input of the optical chip; providing a light detector comprising a single channel receiver surface arranged for receiving a measurement light impinging onto said receiver surface from an optical output of the optical chip, and measuring said received measurement light; aligning the emitted source light from the light source to enter the optical input of the optical chip; aligning the measurement light from the optical output of the optical chip back onto the receiver surface; and measuring the measurement light by said light detector; wherein the receiver surface is larger than the emitter surface.

By providing a receiver surface larger than the emitter surface, alignment of the optical chip can be facilitated as described above. For example, the aligning may comprise translating a position of the source light impinging the optical chip relative to the optical input of the optical chip (or translating the chip relative to the source) until the source light enters the optical input of the optical chip. This may already suffice to provide simultaneous alignment of the optical output(s) since the latter has (have) a higher tolerance for misalignment than the optical input as explained above. Optionally, if additional alignment of the optical output is desired, the alignment may comprise a rotation of the chip and/or emitter/receiver surfaces. By rotating around an optical axis between the emitter surface and optical input, the alignment of the source light onto the optical input can be minimally affected.

By arranging redirecting optics in a light path between the output of the optical chip and the receiver surface, part of the light from the optical chip can be redirected towards an alignment sensor for aligning the source light onto the optical chip. The redirecting optics can e.g. be placed in between optical elements such as collimator/objective lenses of an optional imaging system used to image the emitter surface of the light source onto the optical input of the chip and/or the optical output of the chip onto the receiver surface of the detector.

For example, by providing a camera for imaging a marker on a surface of the optical chip, the aligning may comprise adjusting a position of the optical chip until a position of the marker on the optical chip in the camera image overlaps a previously stored target position of the marker. Advantageously, by using the optical input itself as the marker, no additional marker is needed and the alignment of at least the optical input is provided without rotational ambiguity. Rotational alignment of the optical output can be provided by comparing a second marker on the chip with a second stored target position. Advantageously, the second marker can be the optical output.

In case an optical imaging system is applied between the chip and the apparatus' emitting and receiving ports, the same imaging system can be used to monitor the optional markers. Alternatively or in addition, a separate alignment system can be incorporated in the apparatus, without the co-use of any optional optical elements that is used to achieve the optical coupling.

Alternatively or in addition, the chip can be equipped to provide dedicated alignment signals, emitted either from the chip output ports, from the chip input port, or from dedicated alignment ports. For example, an optical reflector circuit connected to the optical input can be provided as part of the optical chip and reflect part of the source light (e.g. specific wavelengths) or reflect only specific alignment light. In this way, the system can operate in two modes: an alignment mode, wherein the optical alignment of the chip is optimized based on the detected alignment signals; and a measurement mode, wherein the source light enters the optical measurement circuit and is emitted from the optical outputs. In case of a reflective chip configuration, i.e. the alignment signals are emitted from the chip single mode optical input, the apparatus can be equipped with redirecting optics such as circulators, beam splitters, etc.

Alternatively or in addition, in one embodiment, a plurality of alignment input ports are provided on the optical chip near the optical input wherein each alignment input port has a known relative position with respect to the optical input and is connected to a distinct combination of one or more alignment output ports to emit a distinct alignment signal from said alignment output ports when light impinges the respective alignment input port. In this way, aligning can be achieved by measuring the distinct alignment signal to determine a location of the source light impinging on the optical chip near the optical input; and adjusting a position of the source light on the optical chip towards to the optical input based on the known relative position between the optical input and the respective alignment input port corresponding to the measured distinct alignment signal. It will be appreciated that if the alignment output ports are positioned nearby or adjacent respective optical outputs, the alignment signal can be detected by the respective receiver surfaces which are relatively large enough to detect also signals emanating from nearby the optical outputs. For example, if the optical input signal is impingent on alignment port N, offset w.r.t the true input port by (dx,dy), the optical outputs may reveal a digital code, where '1' stands for light received from a specific output, and '0' stands for no light received from that output. The generated digital code is unique for each alignment port. Consequently, the digital code reveals to which alignment port the source light is directed, and a translation of the chip by the appropriate (dx,dy) will result in immediate alignment of the chip.

BRIEF DESCRIPTION OF DRAWINGS

These and other features, aspects, and advantages of the apparatus, systems and methods of the present disclosure will become better understood from the following description, appended claims, and accompanying drawing wherein:

DESCRIPTION OF EMBODIMENTS

Figure 1:
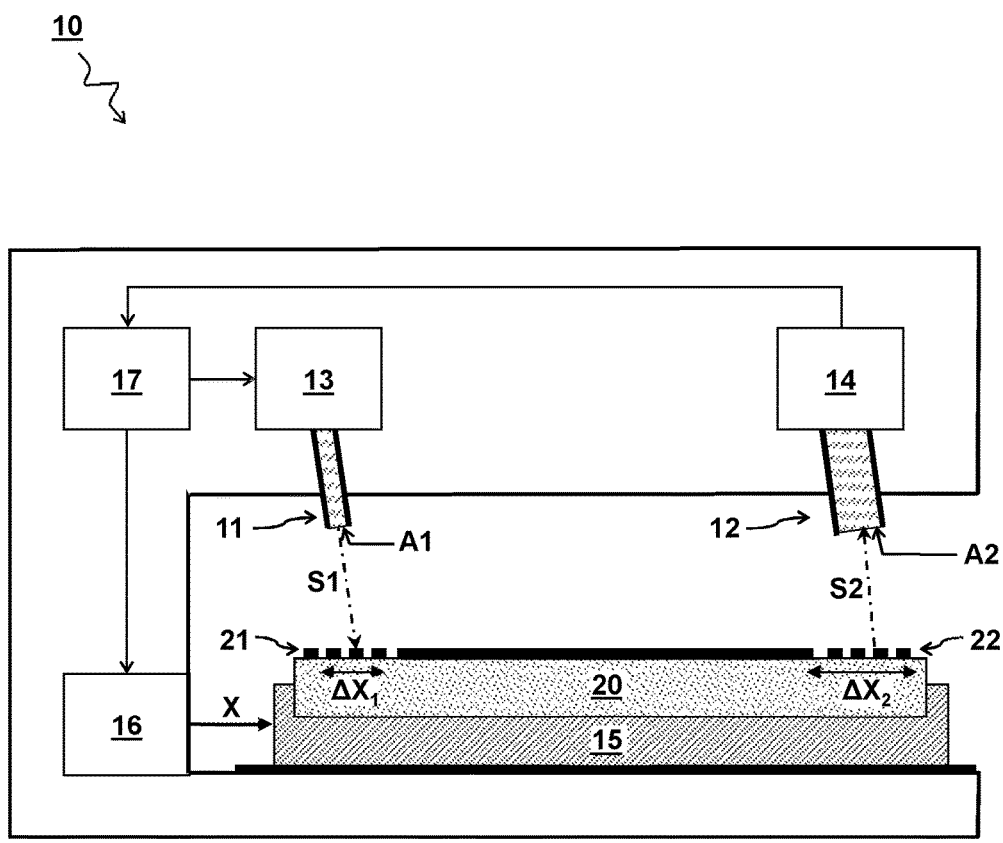
FIG. 1 shows a schematic cross-section view of an embodiment of an apparatus for reading out an optical chip.

Unless otherwise defined, all terms (including technical and scientific terms) used herein have the same meaning as commonly understood by one of ordinary skill in the art to which this invention belongs as read in the context of the description and drawings. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some instances, detailed descriptions of well-known devices and methods may be omitted so as not to obscure the description of the present systems and methods. Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. All publications, patent applications, patents, and other references mentioned herein are incorporated by reference in their entirety. In case of conflict, the present specification, including definitions, will control.

The term 'light' as used herein may comprise all forms of electromagnetic radiation including visible, infrared, and ultraviolet. The light traveling from the light source to the optical chip is generally referred to as the source light or source signal. The light traveling from the optical chip to the light detector generally referred to as the measurement light or measurement signal. The measurement light typically carries information about a parameter of interest measured by interaction of the source light in an optical circuit on the chip. The information may e.g. be carried by one or more of an intensity, frequency, and/or polarization modulation.

The terms 'single-mode' and 'multi-mode' refer to the wave modes of the light. These modes can be regarded as solutions of the Helmholtz equation for waves and may be used to define the way the wave travels in a fibre, in a waveguide or through space. It is noted that waves can have the same mode but different frequencies. For example, in a single mode optical fibre, a plurality of frequencies can be transmitted. A typical single mode optical fibre can have a core diameter between 5 and 15 micrometres. On the other hand, multi-mode optical fibres typically have much larger core diameter, e.g. 40-150 micrometres, i.e. much larger than the wavelength of the light carried in it. An optical fibre has a maximum acceptance projected solid angle "Ω" which is typically dependent on the refractive indices of the core and cladding of the fibre as well as the surrounding medium (typically air). Furthermore, the optical fibre has an acceptance area "A" typically equal to the cross-sectional area of the core. The acceptance projected solid angle "Ω" and acceptance area "A" together define the throughput or etendue "E" of the optical fibre which is roughly proportional to the product A*Ω.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. The description of the exemplary embodiments is intended to be read in connection with the accompanying drawings, which are to be considered part of the entire written description. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

FIG. 1 shows a schematic cross-section view of an embodiment of an apparatus 10 for reading out an optical chip 20.

In one embodiment, the apparatus 10 comprises a chip holder 15 arranged for receiving and holding the optical chip 20. In the shown embodiment, the optical chip 20 can be inserted into a slot of the apparatus 10 and secured in the chip holder 15. The optical chip 20 typically comprises an optical input 21 and an optical output 22. Source light S1 is coupled into the optical input 21 and travels via an optical circuit of the chip (not shown) to the optical output 22. While traversing the optical circuit, the source light may interact with one or more optical sensors (not shown) which can modulate the light depending on a measurement parameter of interest. The resulting measurement light S2 is coupled out of the optical output 22 to be measured by the apparatus 10. The chip holder 15 typically determines a position of the chip 20 and therewith a position of the optical input 21 and optical output 22.

In one embodiment, the apparatus 10 comprises a light source 13 comprising an emitter surface A1. The light source 13 is arranged for emitting source light S1 from the emitter surface A1. The source light S1 is emitted from the emitter surface A1 towards an optical input 21 of the optical chip 20 held by the chip holder 15. In one embodiment, the source light S1 is single mode light for efficient coupling into the optical input 21. In one embodiment, the optical input 21 and/or optical output 22 comprise a vertical grating coupler. In one embodiment, the wavelength and angle of incidence of the source light S1 is adjusted to match the requirements of the grating coupler. In another embodiment (not shown), the light source 13 is an external light source connectable to an input of a light emitter 11 comprised in the apparatus wherein an output surface of the light emitter 11 forms the emitter surface A1.

In one embodiment, the apparatus 10 comprises a light detector 14. The light detector 14 comprises a receiver surface A2. The receiver surface A2 is arranged for receiving measurement light S2 impinging onto said receiver surface A2. Measurement light S2 received on the receiver surface A2 is measured by the light detector 14. For example, an energy and or intensity of the light is measured. In one embodiment, the receiver surface A2 is a single channel receiver surface, i.e. the whole receiver surface corresponds to a single channel of the light detector. In other words, the receiver surface A2 is configured to collect or combine light impinging on the surface light into a single detection channel of the detector. For example, the receiver surface can be regarded as a single integrated detection element. The measurement light S2 is received onto the receiver surface A2 from an optical output 22 of the optical chip 20 held by the chip holder 15. In another embodiment (not shown), the light detector 14 is an external light detector connectable to an output of the light receiver 12 comprised in the apparatus wherein an input surface of the light receiver 12 forms the receiver surface A2

In one embodiment, the apparatus 10 comprises an alignment system 16. The alignment system 16 is arranged for controlled movement X of the chip holder 15 relative to the emitted source light S1. In this way the emitted source light S1 from the light source 13 can be aligned to enter the optical input 21 of the optical chip 20. Simultaneously or consecutively, the measurement light S2 from the optical output 22 of the optical chip 20 can be aligned back onto the receiver surface A2 for measuring the measurement light S2. In one embodiment, the alignment system 16 comprises an actuator for translating and/or rotating the chip holder 15 with respect to the emitter surface A1 and/or receiver surface A2. Alternatively or in addition, the alignment system 16 comprise an actuator for translating and/or rotating a position and/or angular direction of one or both of the emitter surface A1 and/or receiver surface A2 with respect to the chip holder 15. In one embodiment, the alignment system 16 comprises one or more alignment sensors (not shown here) to detect an alignment status of the optical input 21 with respect to the source light S1 and/or an alignment status of the receiver surface A2 with respect to the measurement light S2.

Advantageously, the receiver surface A2 is larger than the emitter surface A1. In other words, an entry aperture A2 of light detector 14 is larger than an exit aperture A1 of the light source 13. In this way an alignment tolerance $\Delta X_2$ of the optical receiver 12 with respect to the optical output 22 can be greater than an alignment tolerance $\Delta X_1$ of the optical emitter 11 with respect to the optical input 21. In other words, the alignment accuracy of the optical output 22 with respect to the receiver surface A2 of the light detector 14 is less critical than that of the optical input 21 with respect to the emitter surface A1 of the light source 13.

In one embodiment, the light source 13 is arranged to emit the source light via a first optical fibre 11. Accordingly, the emitter surface A1 of the light source 13 is an end surface of first optical fibre 11. In one view, the first optical fibre 11 may be regarded as part of the light source 13 in that all light exiting the light source 13 towards the optical chip 20 travels via the first optical fibre 11 which is directly connected to the light source 13.

In one embodiment, the light detector 14 is arranged to receive the measurement light S2 via a second optical fibre 12 Accordingly, the receiver surface A2 is an end surface of the second optical fibre 12. In one view, the second optical fibre 12 may be regarded as part of the light detector 14 in that all light entering the light detector 14 from the optical chip 20 travels via the second optical fibre 12 which is directly connected to the light detector 14.

In one embodiment, the first optical fibre 11 comprises single-mode fibre and the second optical fibre 12 comprises a multi-mode fibre. Accordingly, the receiver surface A2 of the second optical fibre 12 is larger than the emitter surface A1 of the first optical fibre 11.

In one embodiment, one or more of the light source 13, light detector 14, and/or alignment system 16 are controlled by a controller 17. In one embodiment, the controller is comprised in the apparatus 10. Alternatively, the apparatus 10 is connected to an external controller. In one embodiment, the controller is arranged to control the light source 13 to emit light when the optical chip 20 is placed in the chip holder 15. In one embodiment, the controller 17 is arranged to receive a measurement signal from the light detector 14 which is indicative of the measurement light S2 received from the optical chip 20. In one embodiment, the controller 17 is arranged to translate the measurement signal into a measurement parameter measured by a sensor on the optical chip 20. In one embodiment, the controller 17 is arranged to communicate with a feedback device, e.g. a display on the apparatus (not shown), to provide a user feedback of a measured parameter value.

Figure 2:
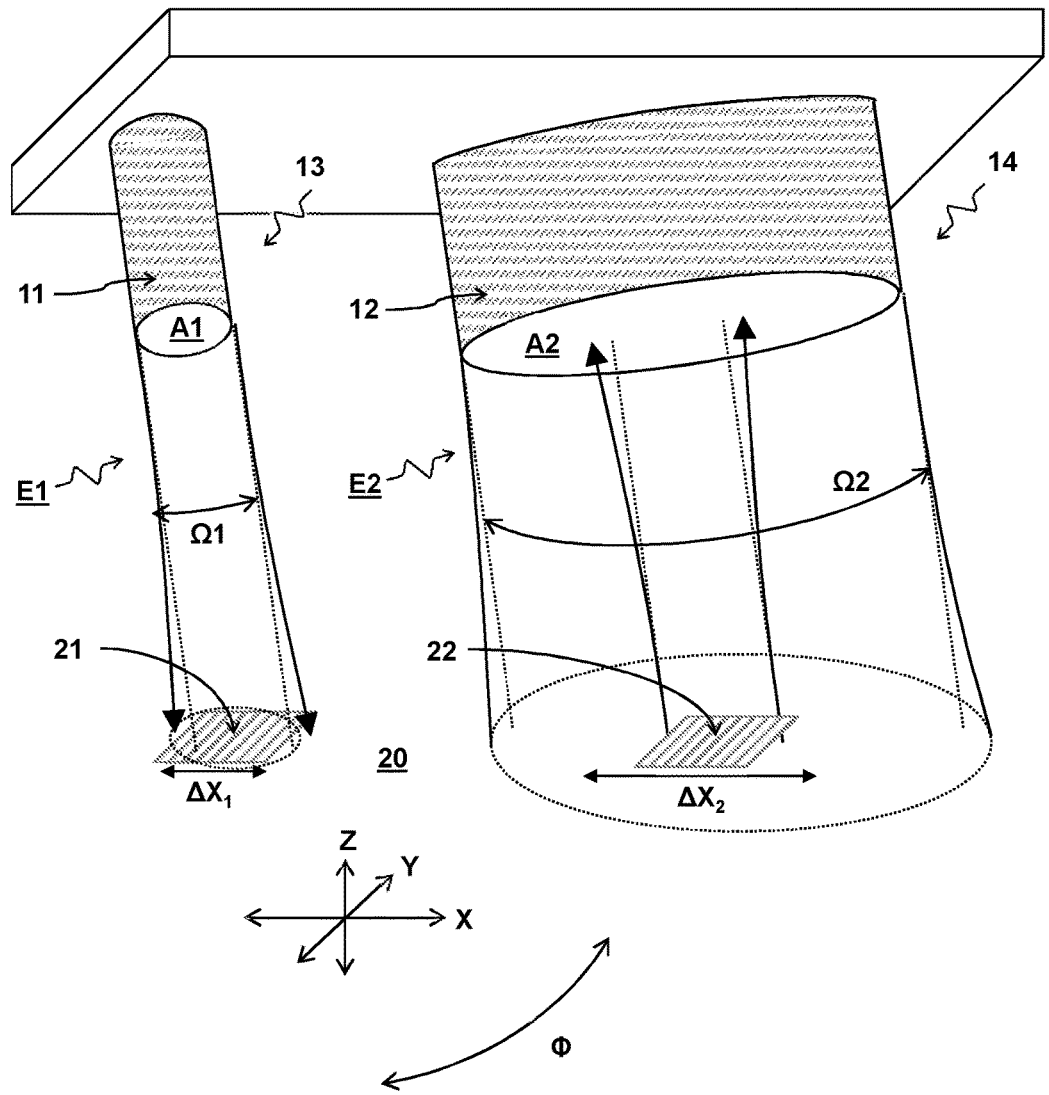
FIG. 2 shows a schematic perspective view of a schematic embodiment of the light source and light detector.

FIG. 2 shows a schematic perspective view of a schematic embodiment of the light source 13 and light detector 14 aligned with an optical input 21 and optical output 22, respectively, of an optical chip 20.

In one embodiment, the light source 13 is arranged to emit the source light S1 from the emitter surface A1 into an emitter solid angle $\Omega 1$ to reach the optical chip 20. In one embodiment, the optical receiver 12 is arranged to receive the measurement light S2 from the optical chip 20 onto the receiver surface A2 from a receiver solid angle $\Omega 2$. Advantageously, in one embodiment, the receiver solid angle $\Omega 2$ is larger than the emitter solid angle $\Omega 1$. This means that the light detector 14 can receive light from a larger solid angle than the solid angle over which the light source 13 emits the light. In other words, in the embodiment it is preferred that the numerical apertures (NA) of the light detector 14 is larger than that of the light source 13.

In one embodiment, the light source 13 is arranged to emit the source light via a first optical fibre 11 wherein the emitter surface A1 is an end surface of first optical fibre 11. In another or further embodiment, the light detector 14 is arranged to receive the measurement light S2 via a second optical fibre 12 wherein the receiver surface A2 is an end surface of the second optical fibre 12. In one embodiment the surface area A2 of the second optical fibre 12 is larger than that of the first optical fibre 11 (A1). In one embodiment the numerical apertures of the second optical fibre 12 is larger than that of the first optical fibre 11. In one embodiment the etendue E2 of the second optical fibre 12 is larger the etendue E1 of the first optical fibre 11.

In one embodiment, an area of the receiver surface or aperture A2 is a factor of two higher than that of the transmitter (A1), preferably, a factor of ten, or even higher, e.g. a factor of hundred. Alternatively or in addition, in one embodiment, a numerical aperture (NA) of the receiver 14 is a factor of two, preferably a factor three higher than a numerical aperture (NA) of the transmitter 14. The NA can e.g. help to accept light emitted from a grating coupler 22 at large angles, and as the grating coupler emission angle is typically wavelength dependent, this may translate into a larger optical bandwidth.

Figure 3:
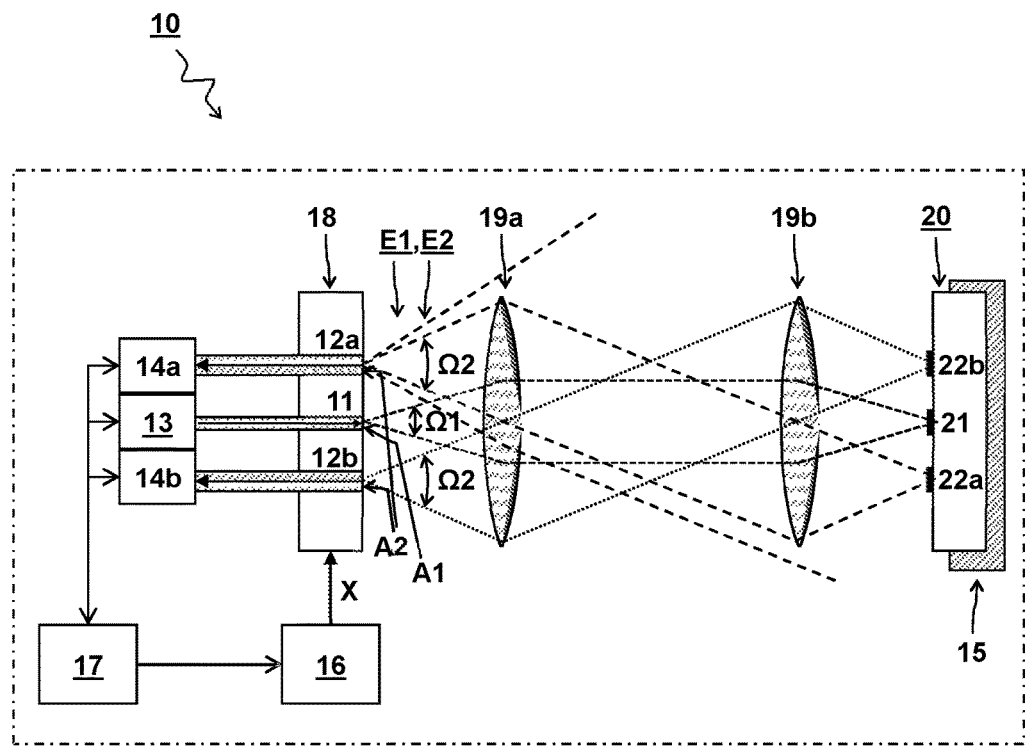
FIG. 3 shows a schematic cross-section view of another embodiment of an apparatus for reading out an optical chip.

FIG. 3 shows a schematic cross section of an embodiment of an apparatus 10 for reading out an optical chip 20.

In one embodiment, the apparatus 10, comprises an imaging system 19a,19b arranged between the emitter surface A1 and the optical chip 20. The optical chip 20 is held by the chip holder 15. In one embodiment, the imaging system 19a,19b is also arranged between the optical chip 20 and the receiver surface A2. In another embodiment (not shown) separate imaging systems are used between the emitter surface A1 and optical input 21 and between the optical output 22 and receiver surface A2, respectively. In one embodiment, the imaging system 19a,19b is arranged for imaging the emitter surface A1 onto the optical input 21 of the optical chip 20. In another or further embodiment, the imaging system 19a,19b is arranged for imaging the optical output 22 of the optical chip 20 in the chip holder 15 onto the receiver surface A2. With the term 'imaging' is generally meant that an object in an object plane of an imaging system is imaged in an image plane of the imaging system with an appropriate magnification factor. In one embodiment, the magnification factor is unity. In another embodiment, the magnification is smaller or larger than unity. In another embodiment, the magnification for imaging A1 onto optical input 21 (or vice versa) is not equal to the magnification for imaging A2 onto optical output 22 (or vice versa).

In one embodiment, the light source 13 is arranged to emit the source light S1 from the emitter surface A1 via the imaging system 19a,19b towards the optical chip 20 into an effective emitter solid angle $\Omega 1$. In one embodiment, the light detector 14 is arranged to receive the measurement light S2 via the imaging system 19a,19b onto the receiver surface A2 from an effective receiver solid angle $\Omega 2$. In one embodiment, the product E2 of the receiver surface A2 times the effective receiver solid angle $\Omega 2$ ("A$\Omega$ product") is larger than the product E2 of the emitter surface A1 times the effective emitter solid angle $\Omega 1$.

The term 'effective solid angle' as used herein refers to the extent within which the emitted or received light can fully traverse the imaging system. It is noted e.g. in the shown embodiment that the effective receiver solid angle Ω2 can be limited by an aperture of the imaging system, e.g. the edges of the lenses 19a and/or 19b, rather than a numerical aperture of the fibre 12a. Light outside the effective solid angle can not travers the imaging system. On the other hand the effective emitter solid angle Ω1 shown in the embodiment is only limited by a numerical aperture of the first optical fibre 11 through which the light source 13 emits the light.

In one embodiment, the optical chip 20 comprises a plurality of the optical outputs 22a,22b connected to the optical input 21 via an optical measurement circuit. Correspondingly, in one embodiment, the apparatus 10 comprises a plurality of light detectors 14a, 14b, each with its own receiver surface A2. In one embodiment, each of the receiver surfaces A2 is larger than the emitter surface A1. In one embodiment, the apparatus comprises a plurality of optical fibres 12a,12b for receiving the light. In one embodiment, a first optical fibre 11 for emitting the source light and a plurality of optical fibres 12a,12b for receiving different measurement light signals are arranged in a fibre array 18.

In one embodiment, a position and/or angle of a fibre array 18 is controlled by an alignment system 16 to align the emitter surface A1 with respect to the optical input 21 and/or the one or more receiver surfaces A2 with respect to respective optical outputs 22a,22b. For example, an alignment may be determined by the presence and/or intensity of the received measurement signal. Alternatively or in addition, one or more separate alignment sensors are provided (not shown here). In one embodiment, the position of the chip is controlled by the alignment system while the fibre array remains stationary.

The present disclosure relates to a system to provide a convenient, cost-effective and robust optical coupling between two optical devices 10 and 20, typically being a read-out unit and an optical chip, respectively. A typical configuration comprises one single-mode (SM) connection for optical signals travelling from device 10 to device 20, and several (two in the example below) multi-mode (MM) connections for optical signals travelling from device 20 to device 10.

In this example, device 20 is a waveguide-based optical chip. It has a single mode input 21, and two single mode outputs 22a and 22b. The interfaces of device 20 can be grating couplers, as commonly used in Silicon-On-Insulator chips, they may be facets (cleaved, polished, etc.), or alternatives. Device 10 provides a single mode optical source (for example a laser or super-luminescent LED) which is to be coupled to port 21 on device 20. In the shown embodiment, an imaging system is used to create an image of the fibre interface(s) (fibre array 18) onto device 20, such that port 11 is imaged on port 21. In this way, an efficient optical coupling is established, while maintaining sufficient working space to conveniently exchange various specimen of device 20 without risk of damaging the fibres or devices 20. The most straightforward implementation of a suitable imaging system comprises a collimated beam. The magnification factor is typically unity, but can have any value as desired for the application. The alignment accuracy is preferably sufficient to establish the single mode connection, typically better than a few microns.

In addition, the imaging system simultaneously images outputs 22a and 22b onto ports 12a and 12b. If these ports are used for power detection only, multi-mode fibres can be used to connect to device 10. Now the alignment accuracy only needs to be sufficient to image the small single mode ports 22a and 22b somewhere in the large core of the multi-mode fibres corresponding to ports 12a and 12b, respectively, and is typically tens of microns. Consequently, only one port (21) needs to be accurately aligned, while the other ports (22a and 22b) are very tolerant in alignment. This is advantageous to conveniently exchange many specimen of device 20 without having to execute a tedious multi-channel alignment procedure over and over again, including rotation: a single channel alignment is sufficient, and the multimode connections are established without substantial additional effort. Moreover, it relaxes the fabrication tolerance for the fibre interface 18, typically a V-groove configuration. Typically, the fibre interface is a row of fibres, accurately positioned in a V-groove chip. Other implementations may involve a 2-dimensional arrangement of fibres, rather than a 1-dimensional.

If the interfaces of device 20 are grating couplers, device 20 can be positioned at the appropriate angle with respect to the optical system (or the other way round). Coupling to and from grating couplers can be done from the top side or from the bottom side of device 20, i.e. the optical path may involve a passage through the substrate of device 20. Alignment may be done manually, or may be automated to any level. Alignment may be actively maintained over long periods of time. The alignment can be done by using a vision system, by monitoring the actual signals, or by monitoring dedicated control signals from dedicated connections between devices 10 and 20.

Figure 4A:
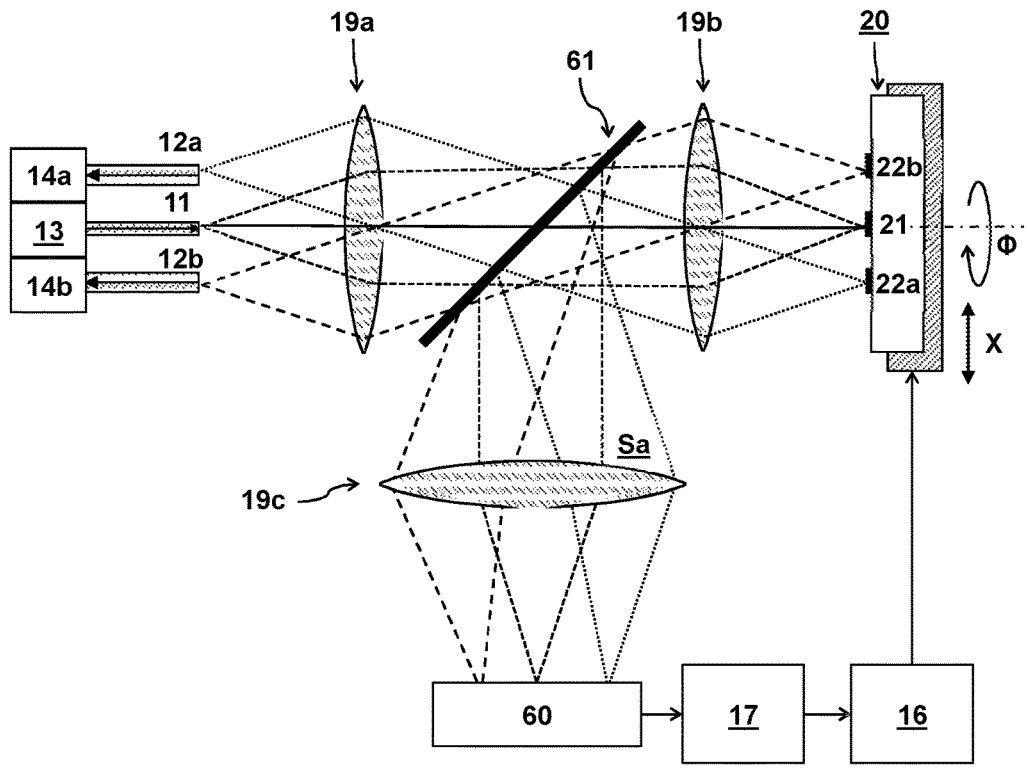
FIG. 4A shows a schematic cross-section view of another embodiment of an apparatus for reading out an optical chip.

FIG. 4A shows a schematic cross section of another embodiment of an apparatus 10 for reading out an optical chip 20.

One aspect of the present disclosure provides a method for reading out an optical chip 20. The method comprises receiving and holding the optical chip 20. The method further comprises providing a light source 13 comprising an emitter surface A1. The light source 13 is arranged for emitting single mode source light S1 from said emitter surface A1 towards an optical input 21 of the optical chip 20. The method further comprises providing a light detector 14 comprising a single channel receiver surface A2 arranged for receiving a measurement light S2 impinging onto said receiver surface A2 from an optical output 22 of the optical chip 20. The method further comprises measuring said received measurement light S2. The method further comprises aligning the emitted source light S1 from the light source 13 to enter the optical input 21 of the optical chip 20. The method further comprises aligning the measurement light S2 from the optical output 22 of the optical chip 20 back onto the receiver surface A2; The method further comprises measuring the measurement light S2 by said light detector 14. Advantageously, the receiver surface A2 is larger than the emitter surface A1.

In one embodiment, the aligning comprises translating a position X of the source light S1 impinging the optical chip 20 relative to the optical input 21 of the optical chip 20 to have the source light S1 enter the optical input 21 of the optical chip 20, or to translate the chip to achieve the same. In another or further embodiment, the aligning comprises rotating a position of the optical output 22 over an angle Φ around a centre of the optical input 21 and/or rotating a position of the receiver surface A2 over an angle −Φ around a centre of the emitter surface A1 for aligning the measurement light S2 from the optical output 22 of the optical chip 20 back onto the receiver surface A2 while maintaining alignment of the source light S1 onto the optical input 21.

In one embodiment, an imaging system 19a,19b is provided between the optical emitter 11 and the optical chip 20 and/or between the optical chip 20 and the optical receiver 12. In one embodiment, the imaging system 19a,19b images the emitter surface A1 of the optical emitter 11 onto the optical input 21 of the optical chip 20 and/or images the optical output 22 of the optical chip 20 onto the receiver surface A2 of the optical receiver 12.

In one embodiment, the apparatus comprises redirecting optics 61, e.g. a beam splitter, dichroic mirror or other optical element to redirect at least part of the light. In one embodiment, the redirecting optics can be inserted or removed from the optical imaging system 19a and 19b, either manually or by means of an actuator. The redirecting optics 61 are arranged for redirecting at least part of the light Sa from the optical chip 20 towards an alignment sensor 60. In this way the source light S1 can be aligned onto the optical chip 20.

In one embodiment, the imaging system comprises a collimator 19a arranged for collimating light from the emitter surface A1. In another or further embodiment the imaging system comprises an objective 19b arranged for imaging the collimated light onto the optical chip 20. The collimator 19a and/or objective 19b may e.g. comprise a lens or curved mirror. In one embodiment, the redirecting optics 61 are arranged in the imaging system, e.g. between the collimator 19a and objective 19b. The redirecting optics 61 is preferably placed in a collimated part of the light beam Sa.

In one embodiment, the alignment sensor 60 comprises a camera arranged for imaging a marker on a surface of the optical chip 20. For example, the aligning comprises adjusting a position of the optical chip 20 until a position of the marker on the optical chip 20 in the camera image overlaps a previously stored target position of the marker.

For example, in order to align the fibres with the integrated circuit (IC) a camera can be used to image part of the chip on a screen. Projected on this screen are markers (the correct position of which are obtained by a single calibration step) and the system is designed such that it actuates the IC until the markers are aligned with the optical interface in the image. Once this is achieved alignment of the fibres can be achieved. In order for the camera to image the chip, it can use the same objective lens. The optical path of the fibres and the alignment camera are combined using a beam splitter (BS). In case a visible light camera is used a dichroic mirror (DM) may be used instead of a beam splitter (may result in a factor 2 more power reaching the IC). In case that an infrared (IR) camera is used (which has the advantage that the IC can be illuminated from the back, since silicon is transparent for IR, such that the front of the IC is fully available for sensing functionality) a beam splitter can be used. In one embodiment the alignment system employs dedicated imaging optics, i.e. not necessarily the same imaging optics as is used for the optical coupling. This may be especially beneficial in case a different optical coupling system is used than as depicted in FIG. 4A, e.g. not employing lenses 19a and 19b. Particularly for highly miniaturized implementation. For example the source 13 may be connected to a fibre with a Graded Index Lens (GRIN lens) to have good optical coupling over a distance up to a few mm, while no optical element is inserted between the emitting port 22 and the receiver 14. If the area A2 of the receiver 14 is sufficiently large, still satisfactory coupling can be achieved. For example, the emitter 13 and receivers 14 may be implemented in a single unit, for example a glass block, or a single opto-electronic chip comprising Vertical Cavity Surface Emitting Lasers (VCSELs) or edge-emitting lasers, or any suitable assembly, where the emitting and/or receiving ports are equipped with micro lenses.

Figure 4B:
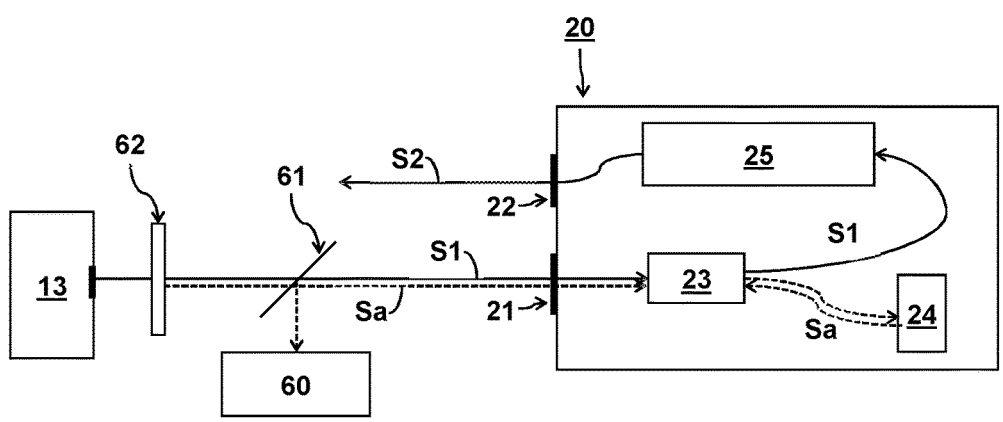
FIG. 4B shows a schematic diagram of an optical circuit as part of an optical chip.

FIG. 4B shows a schematic diagram of an optical circuit as part of an optical chip 20.

In one embodiment, the optical chip 20 comprises an optical reflector circuit 23,24 arranged for reflecting alignment light Sa entering the optical input 21 back out of the optical input 21. In one embodiment, the alignment light Sa is steered onto an alignment sensor 60, e.g. by means of redirecting optics 61. In one embodiment, alignment of the optical input 21 with is determined by measuring said reflected alignment light Sa. In one embodiment, the same light source 13 is used to emit both the source light S1 and the alignment light Sa.

In one embodiment, the alignment signal Sa is distinguished by the optical reflector circuit 23,24 from the source light S1 by one or more of a distinct wavelength and/or polarization. In one embodiment, a polarization altering element 62 such as a lambda half plate is inserted in the light path of the source light S1 to variably alter the polarization in an aligning mode compared to a measuring mode.

For example in one method, a laser is tuned to a dedicated wavelength used only during alignment. Light that is incident on the input vertical grating coupler (VGC) is split on-chip. Part of the light is directed towards the sensors (not used during alignment) and part is directed to a reflector that reflects only the alignment wavelength and nothing otherwise. During alignment the optical IC is actuated stepwise in X and Y until light is received back from the chip indicating that the light is indeed coupled into the input VGC and reflected back from the reflector. Once proper in-coupling is achieved, the wavelength of the laser is tuned to a (range) that is used to interrogate the sensors. Then the output VGS's are monitored while the optical IC is rotated around the optical axis until light is received from the output VGCs, indicating that proper out-coupling is achieved. The reflector may be implemented as a Bragg grating.

In another embodiment, the alignment light (having for example a specific wavelength) is directed to dedicated output ports 22, such that during alignment with this specific wavelength it is known which chip outputs 22 should emit a signal. Alignment is then optimized based on those output ports. This can have the advantage that no additional optics 61 or 62 may be needed, allowing for a high degree of miniaturization.

In another example a photonic crystal is used as input grating. This grating can have the property that TE polarized light is directed in one direction and TM polarized light is converted to TE and directed in another direction. During alignment a lambda half plate is inserted in the optical path (or rotated), changing input polarization from TE to TM, the TM-polarized light is coupled towards a reflector and, similar to the previous example, the optical IC is manipulated until light is received back. Once proper in-coupling is achieved, the half lambda plate is removed (or rotated back), such that TE-polarized light is incident on the input VGC, which is directed towards the sensors. Subsequently, the output VGS's are monitored while the optical IC is rotated around the optical axis until light is received from the output VGCs, indicating that proper out-coupling is achieved.

Figure 5A:
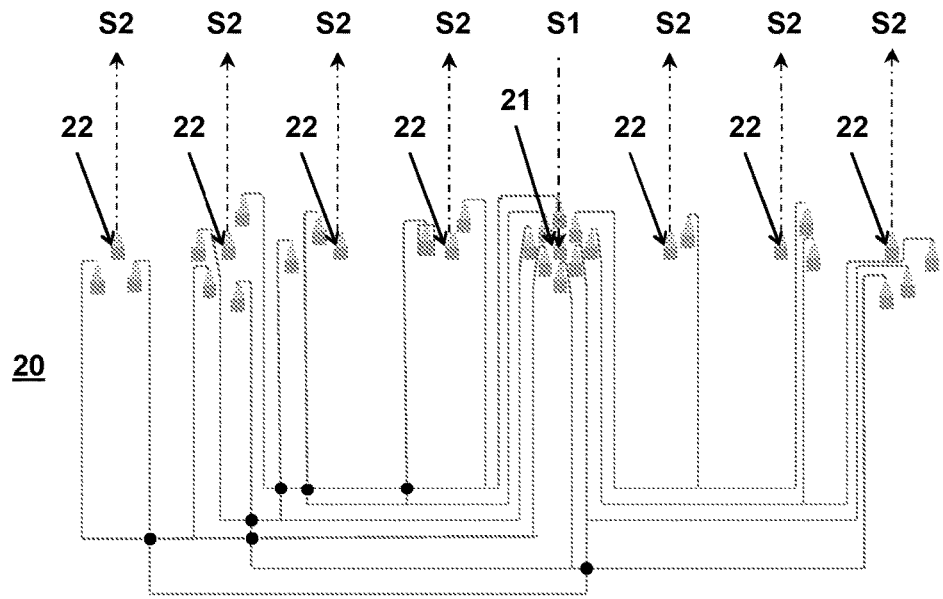
FIGS. 5A and 5B show another schematic optical circuit as part of an optical chip.
Figure 5B:
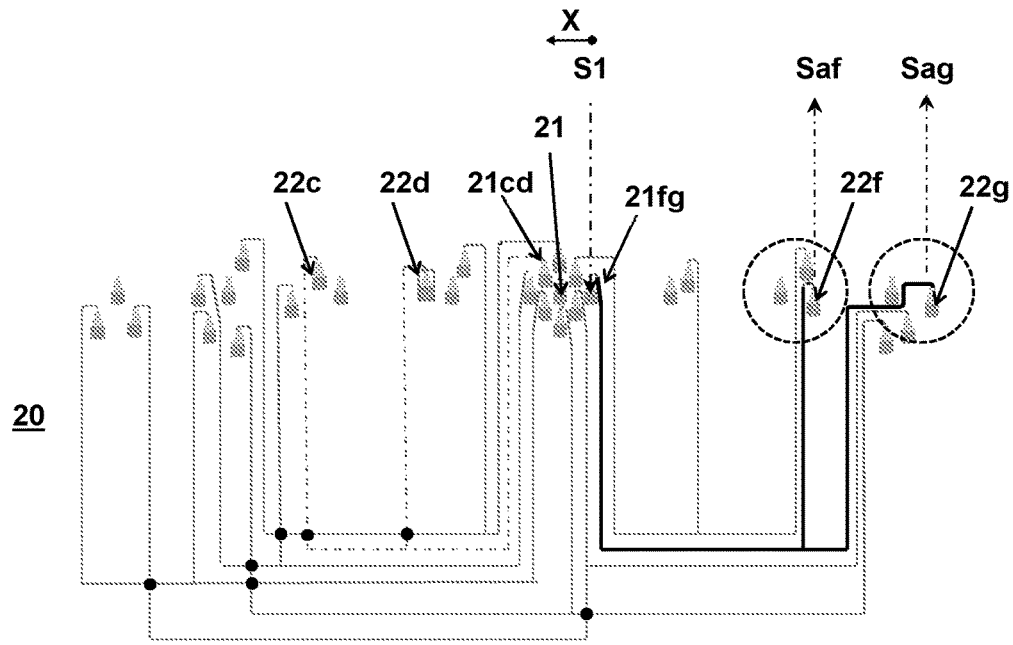

FIGS. 5A and 5B show a schematic optical circuit part of an optical chip for aligning the chip.

In one embodiment, the optical chip 20 comprises a plurality of alignment input ports 21cd,21fg near the optical input 21. Each alignment input port 21fg has a known relative position with respect to the optical input 21. Furthermore each alignment input port 21fg is connected to a distinct combination of one or more alignment output ports 22f,22g to emit a distinct alignment signal Saf and Sag from said alignment output ports 22f,22g when light impinges the respective alignment input port 21fg.

In one embodiment, the aligning comprises measuring the distinct alignment signal Saf and, Sag to determine a location of the source light S1 impinging on the optical chip 20 near the optical input 21; and adjusting a position X of the source light S1 on the optical chip 20 towards to the optical input 21 (or adjusting the position of the chip accordingly) based on the known relative position between the optical input 21 and the respective alignment input port 21fg corresponding to the measured distinct alignment signal Saf and Sag.

FIG. 5A shows a situation wherein the source light S1 is properly aligned onto the optical input 21 of the optical chip 20. The signal received at input 21 is directed to the optical circuit (not shown). FIG. 5B shows a situation wherein the source light S1 is improperly aligned and impinges the alignment input port 21fg which is next to the optical input 21. Because of its connection to the alignment output ports 22f, 22g, this results in an alignment signal Saf, Sag being emitted from the respective alignment output ports 22f, 22g. Because it is known that the signal ports 22f and 22g corresponds to the alignment input port 21fg which is to the right of the optical input 21, the alignment system can bring the chip into alignment by moving the source light S1 to the left and/or the chip 20 to the right.

As another example, if light would hit the alignment input port 21cd shown in FIG. 5B, this would result in another alignment signal comprising light being emanated from alignment output ports 22c and 22d. Again this unique alignment signal can be linked to the known relative position of the alignment input port 21cd with respect to the optical input 21 and the position of the source light S1 and/or optical chip 20 adjusted accordingly. It will be appreciated that the alignment input ports form a grid surrounding the optical input 21, so any light falling in the vicinity of the optical input 21 will result in a unique alignment signal. In one embodiment, the alignment output ports are arranged adjacent or near the optical outputs 22. In this way the light emitted from the alignment output ports can be received by the respective receiver surfaces that also detect the measurement light S2 and no additional alignment sensors are needed. In one embodiment, only alignment signals (for example specific wavelengths) are directed to the alignment ports.

In one embodiment, as shown, each alignment input port is connected to at least two alignment output ports. In this way, a distinction can be made between light not falling on any of the alignment input ports and a situation wherein one of the connection between the alignment input port 11nd alignment output ports is broken. It will be appreciated that the number of alignment input ports can be increased depending on the possible number of unique combinations of alignment output ports that can be addressed. For example: it can be calculated that for one optical input 21 and 7 optical outputs 22, wherein 2 ports should always be lighted, there are 21 unique combinations. Similarly, if always 3 or 5 ports are lighted, there are 35 unique combinations. For an arbitrary number of lighted ports, there can be 126 combinations.

Figure 6A:
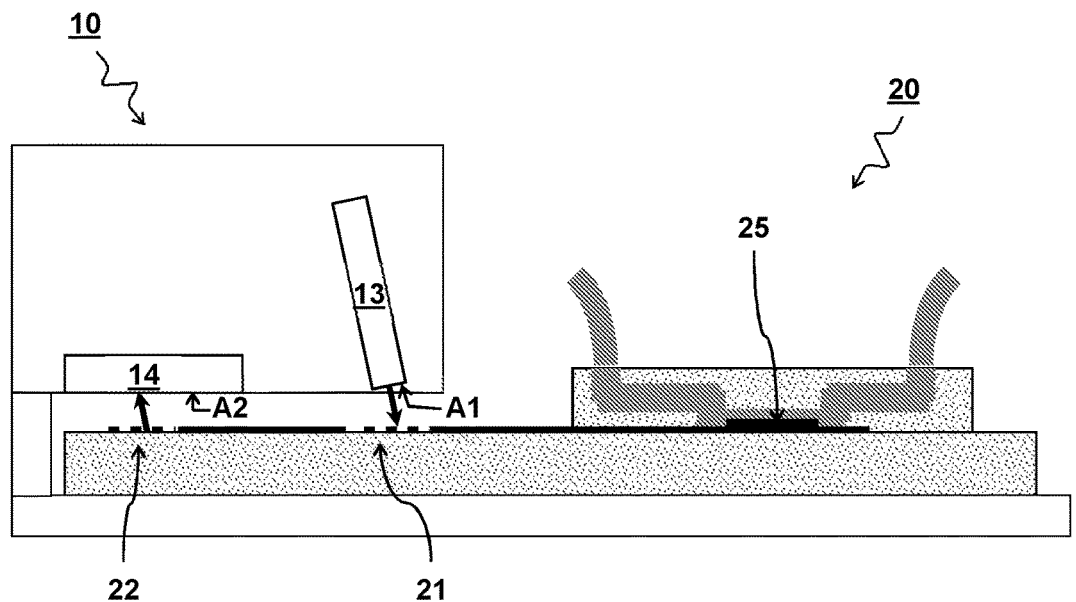
FIGS. 6A and 6B show cross-section views of other schematic embodiments of the apparatus.

FIG. 6A shows a cross-section view of another schematic embodiment of the apparatus 10. In the embodiment, the chip 20 has microfluidics 26,27 on top (where the waveguides are). For example, a fluid inlet 26 and outlet 27, carry a fluid to be analysed past a sensor 25 such as a ring resonator that is part of an optical circuit of the chip 20. Optical coupling is upwards, the couplers are outside the micro fluidics area. A read-out assembly 10 hovers over the chip. In practice, the chip can be put such that the optical couplers end up in a slit below the read-out assembly. The optical output 21 is directed to a (multi mode) detector 14, which is alignment tolerant. A single-mode laser 13 is aligned with the input 21. In the shown embodiment, this is a small laser, but it could also be a fibre or VCSEL. The read-out assembly 10 itself could also be a single chip with a grating coupler. In one embodiment, an optical system such as depicted in FIGS. 3 and 4 is implemented between the source and receivers on one hand, and the optical chip on the other hand. In another embodiment, detectors 14 and or source 13 are equipped with micro optical elements such as micro lenses or GRIN lenses.

Figure 6B:
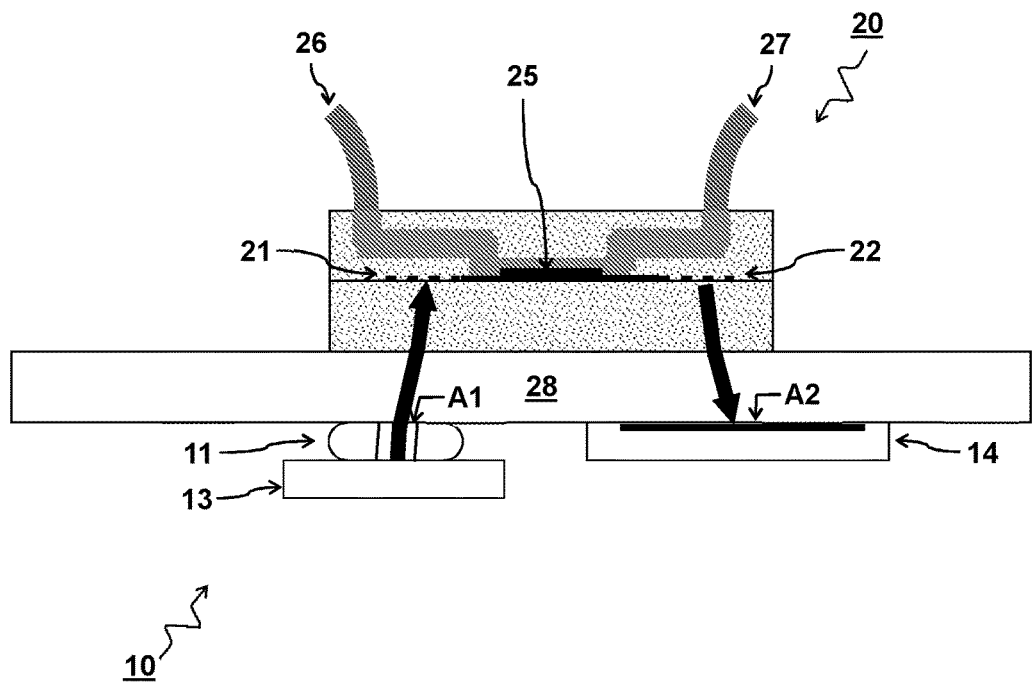

FIG. 6B shows a cross-section view of another schematic embodiment of the apparatus 10. In the embodiment, the chip 20 has microfluidics 26.27 on top (where the waveguides are). Optical coupling is through the chip substrate, so downwards in this view. In the tool 10, the chip 20 rests on a transparent substrate 28 to have a smooth interface (that is, transparent for the measurement signals and possibly for the alignment signals.). The chip outputs 22 are directed to (multi mode) detectors 14 which are alignment tolerant due to its large detection surface. A laser 14 is mounted on the bottom. In the picture it is a VCSEL with some micro optics 11 to shape and direct the (single mode) beam.

For the purpose of clarity and a concise description, features are described herein as part of the same or separate embodiments, however, it will be appreciated that the scope of the invention may include embodiments having combinations of all or some of the features described. For example, while embodiments were shown for free-space chip coupling techniques and complementary alignment strategies, also alternative ways may be envisaged by those skilled in the art having the benefit of the present disclosure for achieving a similar function and result. E.g. optical and/or electrical components may be combined or split up into one or more alternative components. The various elements of the embodiments as discussed and shown offer certain advantages, such as easy alignment of optical devices. Of course, it is to be appreciated that any one of the above embodiments or processes may be combined with one or more other embodiments or processes to provide even further improvements in finding and matching designs and advantages.

It is appreciated that this disclosure offers particular advantages to low-cost point-of-care applications, and in general can be applied for any coupling between optical light sources and/or detectors with optical input/output ports. The free-space chip coupling technique and complementary alignment strategies discussed herein may result in a robust, inexpensive and rapidly established optical coupling and can be suitable for even hand held applications.

While the present systems and methods have been described in particular detail with reference to specific exemplary embodiments thereof, it should also be appreciated that numerous modifications and alternative embodiments may be devised by those having ordinary skill in the art without departing from the scope of the present disclosure. For example, embodiments wherein devices or systems are disclosed to be arranged and/or constructed for performing a specified method or function inherently disclose the method or function as such and/or in combination with other disclosed embodiments of methods or systems. Furthermore, embodiments of methods are considered to inherently disclose their implementation in respective hardware, where possible, in combination with other disclosed embodiments of methods or systems. Furthermore, methods that can be embodied as program instructions, e.g. on a non-transient computer-readable storage medium, are considered inherently disclosed as such embodiment.

Finally, the above-discussion is intended to be merely illustrative of the present systems and/or methods and should not be construed as limiting the appended claims to any particular embodiment or group of embodiments. The specification and drawings are accordingly to be regarded in an illustrative manner and are not intended to limit the scope of the appended claims. In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. The mere fact that certain measures are recited in mutually different claims does not indicate that a combination of these measures cannot be used to advantage. In particular, all working combinations of the claims are considered inherently disclosed.

The invention claimed is:

1. Apparatus for reading out an optical chip, the apparatus comprising
   a chip holder arranged for receiving and holding the optical chip;
   a light source comprising an emitter surface, said light source arranged for emitting single mode source light from said emitter surface towards an optical input of the optical chip held by the chip holder;
   a light detector comprising a single channel receiver surface arranged for receiving and combining measurement light impinging onto said receiver surface in a single detection channel of the light detector for measuring said received measurement light in the single detection channel, wherein the measurement light impinging onto said receiver surface is received from an optical output of the optical chip held by the chip holder;
   an alignment system arranged for controlled movement of the chip holder relative to the emitted source light for aligning the emitted source light from the light source to enter the optical input of the optical chip and for aligning the measurement light from the optical output of the optical chip back onto the receiver surface for measuring the measurement light; wherein
   the receiver surface is larger than the emitter surface.

2. Apparatus according to claim 1, wherein
   the light source is arranged to emit the source light via a first optical fibre wherein the emitter surface is an end surface of first optical fibre; and
   the light detector is arranged to receive the measurement light via a second optical fibre wherein the receiver surface is an end surface of the second optical fibre.

3. Apparatus according to claim 2, wherein the first optical fibre comprises a single-mode fibre and the second optical fibre comprises a multi-mode fibre.

4. Apparatus according to claim 1, wherein
   the light source is arranged to emit the source light from the emitter surface into an emitter solid angle to reach the optical chip; and
   the optical receiver is arranged to receive the measurement light from the optical chip onto the receiver surface from a receiver solid angle; wherein
   the receiver solid angle is larger than the emitter solid angle.

5. Apparatus according to claim 1, comprising an imaging system between the emitter surface and the optical chip held by the chip holder and between the optical chip and the receiver surface, the imaging system arranged for in use imaging the emitter surface onto the optical input of the optical chip in the chip holder and arranged for in use imaging the optical output of the optical chip in the chip holder onto the receiver surface.

6. Apparatus according to claim 5, wherein
   the light source is arranged to emit the source light from the emitter surface via the imaging system towards the optical chip into an effective emitter solid angle;
   the light detector is arranged to receive the measurement light via the imaging system onto the receiver surface from an effective receiver solid angle; and wherein
   the product of the receiver surface times the effective receiver solid angle is larger than the product of the emitter surface times the effective emitter solid angle.

7. Method for reading out an optical chip, the method comprising
   receiving and holding the optical chip;
   providing a light source comprising an emitter surface, said light source arranged for emitting single mode source light from said emitter surface towards an optical input of the optical chip;
   providing a light detector comprising a single channel receiver surface arranged for receiving and combining measurement light impinging onto said receiver surface in a single detection channel of the light detector for measuring said received measurement light in the single detection channel, wherein the measurement light impinging onto said receiver surface is received from an optical output of the optical chip held by the chip holder;
   aligning the emitted source light from the light source to enter the optical input of the optical chip;
   aligning the measurement light from the optical output of the optical chip back onto the receiver surface; and
   measuring the measurement light by said light detector; wherein
   the receiver surface is larger than the emitter surface.

8. Method according to claim 7, wherein the aligning comprises
   translating a position of the source light impinging the optical chip relative to the optical input of the optical chip to have the source light enter the optical input of the optical chip; and
   rotating a position of the optical output around a centre of the optical input and/or rotating a position of the receiver surface around a centre of the emitter surface for aligning the measurement light from the optical output of the optical chip back onto the receiver surface while maintaining alignment of the source light onto the optical input.

9. Method according to claim 7, comprising providing an imaging system between the optical emitter and the optical chip and between the optical chip and the optical receiver, wherein the imaging system images the emitter surface of the optical emitter onto the optical input of the optical chip and images the optical output of the optical chip onto the receiver surface of the optical receiver.

10. Method according to claim 7, wherein the imaging system comprises a collimator arranged for collimating light from the emitter surface and an objective arranged for imaging the collimated light onto the optical chip, wherein redirecting optics are arranged between the collimator and objective for redirecting at least part of the light from the optical chip towards an alignment sensor for aligning the source light onto the optical chip.

11. Method according to claim 10, wherein the alignment sensor comprises a camera arranged for imaging a marker on a surface of the optical chip, wherein the aligning comprises adjusting a position of the optical chip until a position of the marker on the optical chip in the camera image overlaps a previously stored target position of the marker.

12. Method according to claim 7, wherein the optical chip comprises an optical reflector circuit arranged for reflecting an alignment signal entering the optical input back out of the optical input onto an alignment sensor for determining an alignment of the optical input by measuring said reflected alignment signal.

13. Method according to claim 12, wherein the alignment signal is distinguished by the optical reflector circuit from the source light by one or more of a distinct wavelength and/or polarization.

14. Method according to claim 7, wherein the optical chip comprises a plurality of the optical outputs connected to the optical input via an optical measurement circuit.

15. Method according to claim 14, wherein
the optical chip comprises a plurality of alignment input ports near the optical input;
each alignment input port has a known relative position with respect to the optical input;
each alignment input port is connected to a distinct combination of one or more alignment output ports to emit a distinct alignment signal from said alignment output ports when light impinges the respective alignment input port; and wherein the aligning comprises
measuring the distinct alignment signal to determine a location of the source light impinging on the optical chip near the optical input; and
adjusting a position of the source light on the optical chip towards to the optical input based on the known relative position between the optical input and the respective alignment input port corresponding to the measured distinct alignment signal.

* * * * *